United States Patent
Conti et al.

(10) Patent No.: US 9,789,211 B2
(45) Date of Patent: Oct. 17, 2017

(54) METHODS AND COMPOSITIONS FOR POSITRON EMISSION TOMOGRAPHY MYOCARDIAL PERFUSION IMAGING

(71) Applicants: Peter S. Conti, Pasadena, CA (US); Shuanglong Liu, Los Angeles, CA (US); Zibo Li, San Gabriel, CA (US)

(72) Inventors: Peter S. Conti, Pasadena, CA (US); Shuanglong Liu, Los Angeles, CA (US); Zibo Li, San Gabriel, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 14/401,470

(22) PCT Filed: Mar. 15, 2013

(86) PCT No.: PCT/US2013/032591
§ 371 (c)(1),
(2) Date: Nov. 14, 2014

(87) PCT Pub. No.: WO2013/172979
PCT Pub. Date: Nov. 21, 2013

(65) Prior Publication Data
US 2015/0132222 A1 May 14, 2015

Related U.S. Application Data

(60) Provisional application No. 61/646,758, filed on May 14, 2012.

(51) Int. Cl.
*A61K 51/08* (2006.01)
*A61K 51/04* (2006.01)
*A61K 49/04* (2006.01)
*A61B 6/03* (2006.01)
*A61B 6/00* (2006.01)

(52) U.S. Cl.
CPC .......... *A61K 51/044* (2013.01); *A61B 6/037* (2013.01); *A61B 6/503* (2013.01); *A61K 49/04* (2013.01); *A61K 51/0482* (2013.01); *A61K 51/0497* (2013.01); *A61K 51/088* (2013.01)

(58) Field of Classification Search
CPC ........ A61K 51/00; A61K 49/10; A61K 51/04; A61K 51/08
See application file for complete search history.

(56) References Cited

U.S. PATENT DOCUMENTS

| | | | | |
|---|---|---|---|---|
| 2007/0092442 | A1* | 4/2007 | Gambhir | G01N 33/5079 424/1.11 |
| 2008/0267882 | A1* | 10/2008 | Chen | A61K 47/48215 424/9.4 |
| 2009/0214437 | A1* | 8/2009 | Kalyanaraman | A61K 49/103 424/9.33 |
| 2010/0196271 | A1* | 8/2010 | Conti | A61K 51/0482 424/1.69 |

FOREIGN PATENT DOCUMENTS

WO    2011097649 A2    8/2011

OTHER PUBLICATIONS

Chang-Tong Yang et al., Synthesis and Structural Characterisation of Complexes of a DO3A-Conjugated Triphenylphosphonium Cation with Diagnostically Important Metal Ions, Inorg. Chem. 2007, 46, 8988-8997.*
Alan M. Sargeson, The potential for the cage complexes in biology, Coordination Chemistry Reviews, 151, 89-114, 1996.*
Michael P. Murphy, Selective targeting of bioactive compounds to mitochondria, TIBTECH, 15, 326-330, 1997.*
International preliminary report on patentability dated Nov. 27, 2014 issued in corresponding PCT application PCT/US2013/032591.
Wadas et al. Coordinating Radiometals of Copper, Gallilum, Indium, Yttrium, and Zirconium for PET and SPECT Imaging of Disease. Chemical Reviews. 110, 2858-2902. Apr. 23, 2010 entire document.
International Search Report dated Jun. 3, 2013 issued in corresponding PCT application No. PCT/US2013/032591 cites the U.S. Patent Application Publications, Foreign Patent Documents and Non-Patent Literature Documents listed above.

* cited by examiner

*Primary Examiner* — Michael G Hartley
*Assistant Examiner* — Jagadishwar Samala
(74) *Attorney, Agent, or Firm* — DLA Piper LLP (US)

(57) ABSTRACT

This invention provides compounds and compositions useful as imaging tracers for positron emission tomography myocardial perfusion imaging (PET MPI). Compounds in accordance with embodiments of the invention will generally comprise three structural elements: i) a triphenylphosphonium moiety; ii) a chelating element; and iii) a hydrophobic element. The tracer compounds are preferably radiolabeled with $^{64}$Cu or $^{18}$F. Also provided are methods for synthesizing the compounds, methods for derivatizing the compounds, and derivatives thereof.

6 Claims, 8 Drawing Sheets

1. The position of each motif is not fixed. For example, it could be but not limited to the following 2. The linkage between each motif is not limited to amide bond. It could be done using SH double bond reaction, or click reactions.

3. The Cation is not limited to TPP, it could be other $-\overset{\oplus}{P}R_1R_2R_3$, $-\overset{\oplus}{N}R_1R_2R_3$ et al.

METHODS AND COMPOSITIONS FOR POSITRON EMISSION TOMOGRAPHY MYOCARDIAL PERFUSION IMAGING

CROSS-REFERENCE TO RELATED APPLICATIONS

This application is a national stage of international application number PCT/US2013/032591, filed on Mar. 15, 2013 and claims the benefit of Provisional Application No. 61/646,758 filed May 14, 2012, the entire content of which are hereby incorporated herein by reference.

FIELD OF THE INVENTION

The present invention is directed to methods and compositions for positron emission perfusion imaging. More particularly, the present invention provides compositions based on $^{64}$Cu-Sar-TPP imaging probes which comprise three parts: a TPP cation that targets mitochondria, a radiolabel cross-linking agent based on a Sar cage, and a hydrophobic component.

BACKGROUND OF THE INVENTION

Coronary artery disease and its related cardiac disorders represent the most common cause of death in the USA and Western world. Although the recent advancements in treatment have led to improvements in patient outcome, the most critical factor is the correct assignment of these therapy options and the precise treatment evaluation thereafter [1, 2]. Myocardial perfusion imaging (MPI) has demonstrated excellent diagnostic accuracy, superb ability to perform risk stratification, and capability for demonstrating therapeutic benefit when applied in the management of the cardiac patient [1-5]. Recently, MPI advanced further with the addition of hybrid PET/CT and SPECT/CT systems that permit the integration of the presence of coronary artery calcium and the degree of coronary artery luminal narrowing with the impairment in myocardial vasodilator function.
PET-CT and MPI Probes Integrated PET-CT has been widely applied in clinical care as a novel diagnostic imaging tool in patient management owing to its high sensitivity and good resolution. Application of PET-CT has been extended to cardiovascular-related diseases and is undergoing rapid expansion in this area [6-8]. Cardiac PET-CT imaging is advancing the ability to image the structure and function of the heart and vasculature by providing concurrent quantitative information about myocardial perfusion and metabolism with coronary and cardiac anatomy. Precise measurement of regional blood flow has significant clinical importance in identifying ischemia, defining the extent and severity of disease, assessing myocardial viability, establishing the need for medical and surgical intervention, and monitoring the effects of treatments [7, 9]. For myocardial perfusion PET-CT imaging, the positron-emitting radiopharmaceutical must be taken up into the myocardium in proportion to blood flow in order to evaluate areas with reduced blood flow (for example due to ischemia). Several tracers have been used for evaluating myocardial perfusion with PET in clinical practice, including $^{82}$Rb chloride, $^{15}$O-water, and $^{13}$N-ammonia. The short physical half-life of these isotopes allows rapid sequential imaging of rest and stress perfusion. However, the short half-life (from 1-10 min) limits the duration and timing of imaging. Commercial distribution of such agents also is limited, and their associated production costs can be very high. Development of long-lived perfusion imaging agents, labeled with isotopes such as $^{18}$F (T½=110 min) or $^{64}$Cu (T½=12.7 h), could potentially be distributed by unit doses or with kits, and may allow delayed cardiac imaging following administration. In fact, several $^{18}$F labeled tracers are currently being tested in clinical trials for myocardial PET imaging. For example, $^{18}$F-flurpiridaz (also known as $^{18}$F-BMS747158-02) and $^{18}$F-fluorobenzyltriphenylphosphonium ($^{18}$F-FBnTP) have demonstrated their great potential for PET MPI [10-14]. These promising results clearly demonstrated that PET imaging is valuable tool for the management of the cardiac patient, and novel MPI agents need to be developed to complement currently used $^{13}$N—NH$_3$ and $^{82}$Rb. Recently, longer-lived PET isotopes, including Cu-64, have been investigated for myocardial perfusion imaging [15, 16]. Agents such as $^{64/62}$Cu-pyruvaldehyde-bis(N4-methyl-thiosemicarbazone) ([$^{64/62}$Cu]-PTSM) have been developed for PET cardiac imaging. However, this tracer has high liver uptake that results in spillover into the inferior wall of myocardial. Moreover, this tracer clears slowly from the blood pool due to the association with serum albumin [16].
Uptake of Triphenylphosphonium (TPP) Cations by Mitochondria There is a great need to develop novel PET myocardial perfusion imaging agents with optimal imaging property and longer radioactive half-lives than conventional PET MPI agents. Recently, radiolabeled triphenylphosphonium (TPP) ion exhibited optimal characteristics as a PET imaging perfusion tracer due to its significant heart uptake and kinetics [17-20]. The biophysics of the movement of TPP cations across phospholipid bilayers has been extensively studied and is well understood [21, 22]. It has been shown that specific molecular transport methods are not necessary for TPP compounds, which display extensive binding to the matrix surface of the mitochondrial inner membrane [23-25]. A critical parameter affecting the rate and extent of uptake of TPP cations is their hydrophobicity [25]. As the hydrophobicity increases, the activation energy for transport of TPP cations across the plasma membrane is lowered, which will greatly enhances the rate of uptake. In summary, the uptake of TPP cation into the organs from the circulation is driven by the hydrophobicity, and plasma/mitochondrial membrane potentials.
Rationale of $^{64}$Cu-TPP Probe Development With 12.7 h half-life and simple labeling procedures, $^{64}$Cu labeled MPI agents could potentially be distributed by unit doses or with kits, and allow delayed cardiac imaging following administration. An ideal $^{64}$Cu labeled MPI probe need to have the high heart uptake, proportional to blood flow with little redistribution, while maintaining low liver and lung uptake. Previously, $^{64}$Cu-radiopharmaceutical has been developed based on TPP ions. However, those bifunctional chelators (BFCs) generally have negatively charged COOH groups (such as DOTA or NOTA), which would decrease the voltage-dependent uptake of TPP based probes. Moreover, $^{64}$Cu-DOTA complexes were found unstable in vivo, which would lead to nonspecific liver uptake [26, 27]. Stable attachment of radioactive $^{64}$Cu$^{2+}$ is therefore another critical factor to consider.

SUMMARY OF THE INVENTION

Accordingly, one object of the present invention is directed to compositions and methods which will permit health professionals to detect areas of the heart muscle that have inadequate blood supply, to quantify the extent of the heart muscle with a limited blood flow, to provide information about the heart's pumping function, to assess the amount of scarring from a heart attack, and to evaluate the results of coronary bypass surgery or angioplasty. The radio-labeled probes (e.g. $^{64}$Cu-TPP probes) of the present invention will not only overcome the production and protocol limitations of currently used radiotracers, but also allow delayed cardiac imaging following administration, which may provide critical information that could not be obtained before.

It is a further advantage of the present invention that the TPP cation could be easily further derivatized through bioconjugation, while the cardiac uptake was still maintained. Thus, one aspect of the invention is directed to TPP cation derivatives and methods for manufacturing thereof.

Another aspect of the present invention is directed to a versatile stable bifunctional chelator for $^{64}$Cu labeling based on the positively charged sarcophagine (Sar) cage. While not intending to be bound by any particular theory, compositions of the present invention generally operate under the following three principles: 1) TPP compounds with suitable hydrophobicity will be taken up by heart muscle; 2) the Sar chelators will form stable complexes with $^{64}$Cu that are stable in vivo; 3) the Sar chelators will link the TPP ion with a hydrophobic moiety, which will lead to a $^{64}$Cu labeled PET MPI agents. Unlike the traditionally used DOTA or NOTA chelators, the positively charged Sar chelator will maintain the zeta potential of the TPP based probe for cardiac imaging. This $^{64}$Cu labeled agent will allow the study of a patient in an extended period of time, which is difficult to do currently by other prior art means. It should be noted that 64Cu labeling is preferred but not the only possible radiolabel. Those skilled in the art will readily recognize that other suitable labels with equivalent properties may include $^{68}$Ga and other equivalents.

One embodiment of the present invention is directed to the design, synthesis, and characterization of novel $^{64}$Cu-Sar-TPP analogues. Multifunctionalized Sar cage are synthesized and conjugated to TPP for mitochondria targeting. In one embodiment, $^{64}$Cu-Sar-TPP imaging probes can be divided into three parts: a TPP cation targeting mitochondria, a radiolabelable cross-linking agent based on Sar cage, and a hydrophobic component. A hydrophobic moiety is introduced at one end of the Sar cage to modify the hydrophobicity of the probe. Another embodiment of the present invention is directed to kits for the synthesis of $^{64}$Cu-Sar-TPP analogues together with instructions for producing the $^{64}$Cu-Sar-TPP analogues in a composition suitable to administration to patients.

Another embodiment of the present invention is directed to methods of in vitro PET myocardial perfusion imaging comprising administration of the $^{64}$Cu-Sar-TPP analogues, and uses thereof as myocardial perfusion PET imaging agents. The synthesized probe should be screened in vitro to test their stability, hydrophobicity, and voltage-dependent uptake to eliminate species not suitable for the following in vivo studies.

Another embodiment of the present invention is directed to in vivo microPET/CT and quantitative autoradiagraphy imaging comprising the administration of the $^{64}$Cu-Sar-TPP analogues in animals, including humans. Suitable $^{64}$Cu-Sar-TPP MPI probe for in vitro and in vivo preferably possess high cardinal uptake, good stability in vivo, and high heart to muscle, heart to liver, heart to lung, and heart to blood ratios. The selected probes will be further evaluated in rats, including a side by side comparison with the well-established $^{13}$N—NH$_3$ and $^{99m}$Tc-Sestamibi agents.

Other aspects and advantages of the present invention will become apparent from the following detailed description, the accompanying drawings, and the appended claims.

DETAILED DESCRIPTION

Definition

Figure 1:
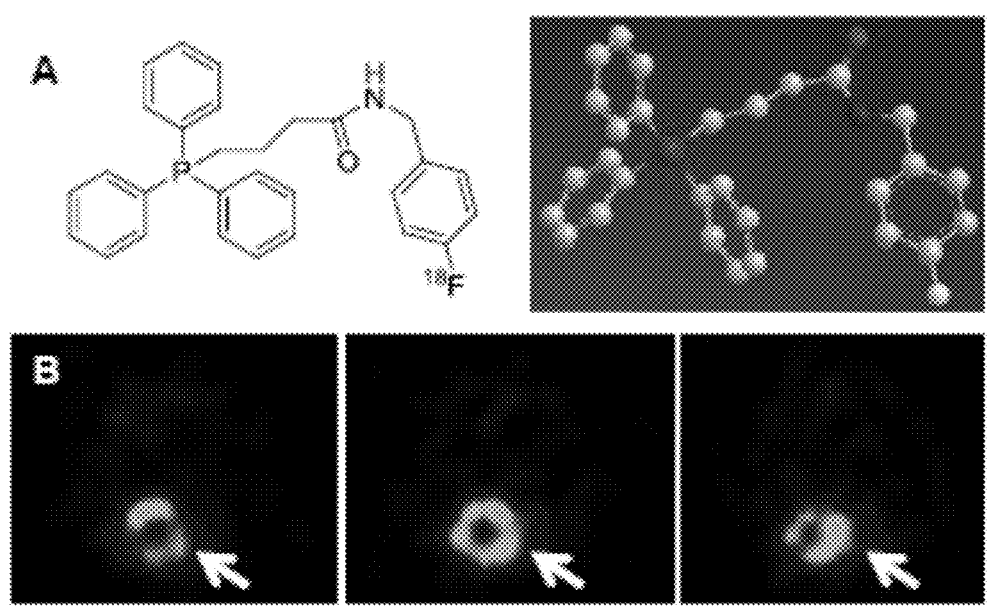
FIG. 1 shows (A) the chemical/Chem3D structure of $^{18}$F-FBN-TPP; (B) microPET imaging of mice after i.v. injection of $^{18}$F-FBN-TPP (2 h time point. Pictures shown represent different slices. Heart is indicated by arrows.

Unless otherwise indicated herein, all terms used herein have the meanings that the terms would have to those skilled in the art of the present invention. Practitioners are particularly directed to current textbooks for definitions and terms of the art. It is to be understood, however, that this invention is not limited to the particular methodology, protocols, and reagents described, as these may vary.

The term "alkyl" herein used means a straight or branched chain alkyl, for example, methyl, ethyl, n-propyl, i-propyl, n-butyl, i-butyl, sec-butyl, tert-butyl, n-pentyl, i-pentyl, neopentyl, tert-pentyl, and the like.

The term "cycloalkyl" herein used is exemplified by cyclopropyl, cyclobutyl, cyclopentyl, cyclohexyl, cycloheptyl, and the like.

Substituents for an alkyl or an alkyl moiety described as "optionally substituted" or compositions described as an "optionally substituted alkyl", "optionally substituted cycloalkyl", are hydroxy, alkoxy (e.g., methoxy and ethoxy), mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, alkoxycarbonyl (e.g., methoxycarbonyl and ethoxycarbonyl), nitro, cyano, haloalkyl (e.g., trifluoromethyl), substituted or unsubstituted amino (e.g., methylamino, dimethylamino, and carbamoylamino), guanidino, phenyl, benzyloxy, carboxylic acid and the like. These substituents are able to bind them at one or more of any possible positions.

The term "aryl" herein used means monocyclic or condensed ring aromatic hydrocarbons. Examples of the aryl are phenyl, naphthyl, and the like. The aryl may be optionally substituted.

The term "aralkyl" herein used means the above mentioned alkyl substituted by the above mentioned aryl at any possible position. Examples of the aralkyl are benzyl, phenethyl, phenylpropyl (e.g., 3-phenylpropyl), naphthylmethyl (.alpha.-naphthylmethyl), anthrylmethyl (9-anthrylmethyl), and the like. Benzyl is preferred. The aryl part may optionally be substituted.

The term "heteroaryl" herein used means a 5 to 6 membered aromatic heterocyclic group which contains one or more hetero atoms selected from the group consisting of nitrogen, oxygen and sulfur atoms in the ring and may be fused with a carbocyclic ring or other heterocyclic ring at any possible position. The aryl part of the above heteroaryl is optionally substituted.

Substituents for the aromatic ring that may be "optionally substituted" or described as an "optionally substituted aryl", "optionally substituted aralkyl", "optionally substituted heteroaryl", "optionally substituted heteroarylalkyl", "optionally substituted arylene", and "optionally substituted heteroarylene" are, for example, hydroxy, alkoxy (e.g., methoxy and ethoxy), mercapto, alkylthio (e.g., methylthio), cycloalkyl (e.g., cyclopropyl, cyclobutyl, cyclopentyl), halogen (e.g., fluoro, chloro, bromo, and iodo), carboxy, alkoxycarbonyl (e.g., methoxycarbonyl and ethoxycarbonyl), nitro, cyano, haloalkyl (e.g., trifluoromethyl), aryloxy (e.g., phenyloxy) substituted or unsubstituted amino (e.g., methylamino, dimethylamino, diethylamino, and benzylidenamino), guanidino, alkyl (e.g., methyl, ethyl, n-propyl, i-propyl, n-butyl, i-butyl, sec-butyl, tert-butyl, n-pentyl, i-pentyl, neo-pentyl, and tert-pentyl), alkenyl (e.g., vinyl and propenyl), alkynyl (e.g., ethynyl and phenylethynyl), alkanoyl (e.g., formyl, acetyl, and propionyl), acyloxy (e.g., acetyloxy), acylamino, alkylsulfonyl (e.g., methylsulfonyl), phenyl, benzyl, an azo group (e.g., phenylazo), optionally substituted heteroaryl (e.g., 3-pyridyl), optionally substituted ureido (e.g., ureido and phenylureido), and the like. These substituents are able to bind to it at one or more of any possible position.

Demonstrative Examples

The following examples are provided in order to demonstrate and further illustrate certain embodiments and aspects of the present invention and are not to be construed as limiting the scope thereof. While such examples are typical of those that might be used, other procedures known to those skilled in the art may alternatively be utilized. Indeed, those of ordinary skill in the art can readily envision and produce further embodiments, based on the teachings herein, without undue experimentation.

Certain Experimental Observations

The TPP Catio May be Functionalized Through Amide Bond Formation while Maintaining Cardiac Uptake.

As a proof-of-concept, $^{18}$F-FBN-TPP (FIG. 1A) was synthesized and its in vivo distribution tested in normal mice. $^{18}$F-FBN-TPP was obtained in ~70% yield with 3.2±1.4 Ci/μmol specific activity. The results of biodistribution and micro-PET imaging studies of $^{18}$F-FBN-TPP in mice showed preferential accumulation in the myocardium (FIG. 1B). The uptake is prominent and persistent. Thus, TPP compounds can be modified through amide bond formation and maintain the myocardial uptake.

Figure 2:
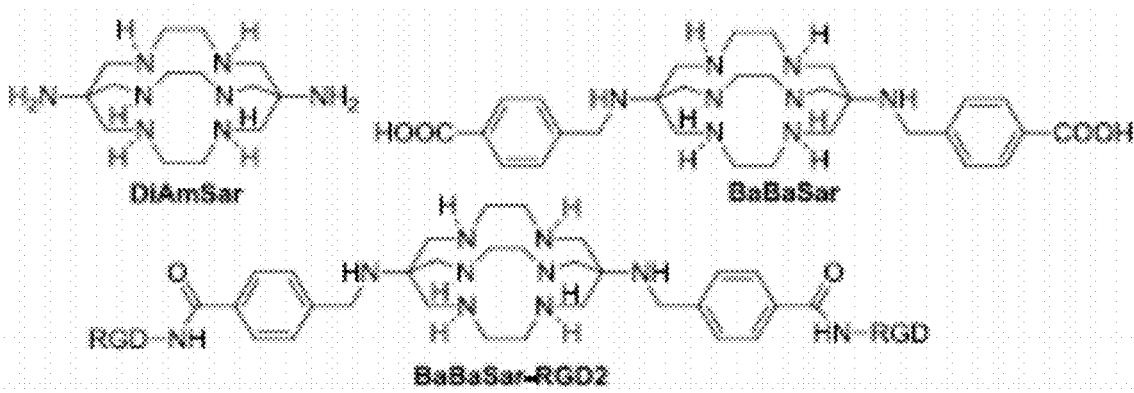
FIG. 2 shows the chemical structures of DiAmSar, BaBaSar, and BaBaSar-RGD2.

Although sarcophagine $^{64}$Cu$^{2+}$ complexes have been demonstrated to be superior to other chelators such as DOTA with respect to in vivo stability, attempts to attach the DiAmSar (FIG. 2) directly to protein using EDC activation has been unsuccessful due to its relatively inert primary amine [32]. In order to overcome this limitation, it is necessary to further derivatize these hexaazamacrobicyclic caged-like BFCs to permit the conjugation of sarcophagine (Sar) with bioligands using conventional synthetic strategies such as amide bond formation. [26, 30] As DiAmSar has two relatively inert primary amines on either end of its cage, novel Sar cage derivatives can be used as radiolabelable cross-linking agents when multifunctional groups are introduced to both ends. The functionalization approach of Sar cage has been improvised through a direct alkylation (SN2) reaction [31]. In order to demonstrate that multifunctional groups could be introduced to the Sar cage by reacting with the relatively inert primary amines, we first synthesized BaBaSar, which has two pendant carboxylate groups at either end of the Sar cage (named BaBaSar). This novel multivalency bifunctional chelator could be further conjugated to multiple targeting ligands (such as RGD peptides) via biologically stable amide bonds [31]. The Cu complex demonstrated good stability in vivo.

Experimental Design and Methods

Experimental Design:

To date, a number of PET MPI probes have been developed for clinical applications. However, many of the tracers may require expensive onsite production and inconvenient on-scanner tracer administration. Unlike commonly used PET MPI agents, a $^{64}$Cu MPI probe not only can overcome the production and protocol limitations of currently used radiotracers, but also can allow delayed cardiac imaging following administration, which may provide critical information that could not be obtained currently. Various TPP compounds with suitable hydrophobicity have been demonstrated to be taken up by heart muscle.

Figure 3:
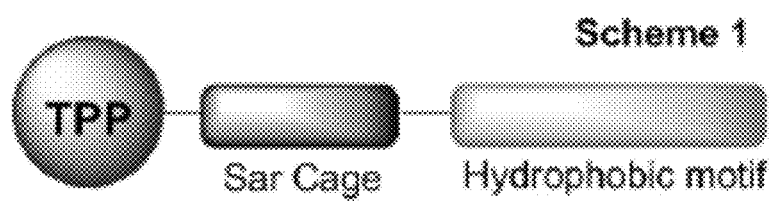
FIG. 3 shows an exemplary schematic representation of a $^{64}$Cu labeled PET MPI agent in accordance with embodiments of the present invention.

We also demonstrated that the cardinal uptake of TPP was maintained after modification with amide bond (FIG. 1). In accordance with embodiments of this invention, the Sar chelators may be introduced to the TPP ion and hydrophobic property thereof may be modified to develop a $^{64}$Cu labeled PET MPI agent (See Scheme 1 in FIG. 3).

It should be noted that the structure and relative positioning of the TPP analog, sar cage and hydrophobic motif is flexible and variable. Other available alternatives include those shown in FIG. 4.

Figure 4:
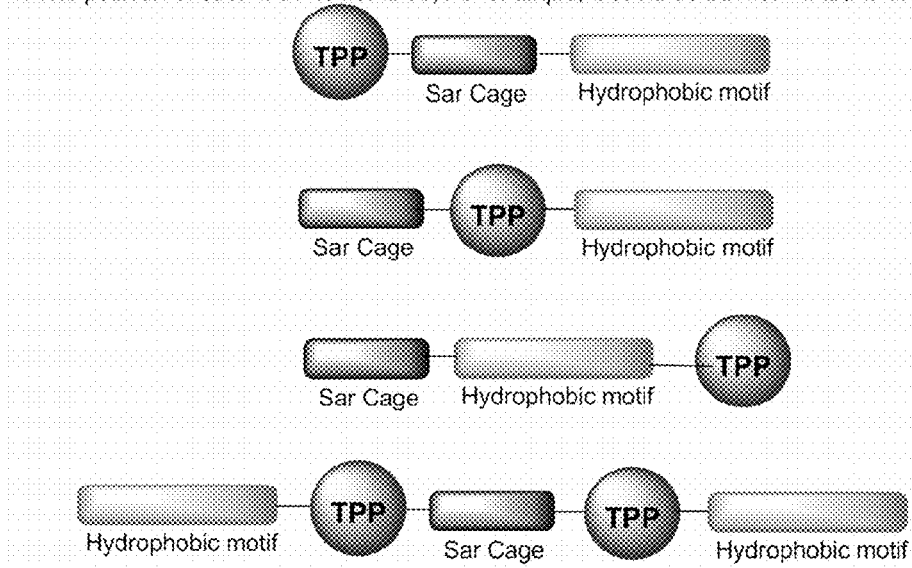
FIG. 4 shows additional exemplary $^{64}$Cu labeled PET MPI agents in accordance with embodiments of the present invention.
Figure 4:
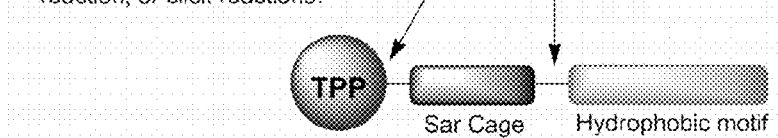
Figure 4:
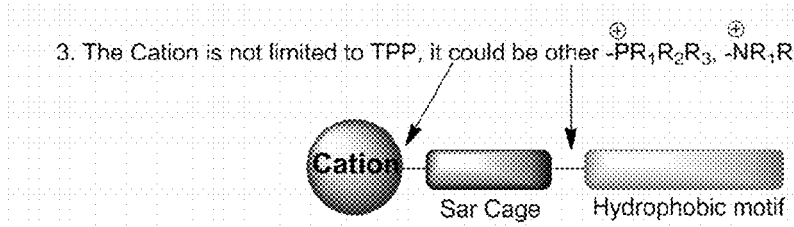

In FIG. 4, $R_1$, $R_2$, and $R_3$ are independently selected from the group consisting of an optionally substituted aryl, an optionally substituted aralkyl, an optionally substituted alkyl, an optionally substituted cycloalky, optionally substituted heteroaryl. Further, the hyrdrophobic motif may be optionally substituted. Unlike the traditionally used DOTA or NOTA chelators, the positively charged Sar chelator will maintain the zeta potential of the TPP probe for cardiac imaging. This $^{64}$Cu labeled agent will allow us to study the patient in an extended period of time, which is difficult to do currently.

The Design, Synthesis, and Characterization of Novel $^{64}$Cu-Sar-TPP Analogues A novel cage-like bifunctional chelator AmBaSar based on sarcophagine for $^{64}$Cu-radiopharmaceuticals [14] has been developed. AmBaSar can form a stable complex with $^{64}$Cu$^{2+}$. Micro-PET imaging of this type of $^{64}$Cu-complex shows very low uptake in liver and lung, potentially beneficial for cardiac imaging. In order to develop a stable $^{64}$Cu-TPP complex, the Sar chelator may be attached to the lipophilic heart targeted TPP cation and a hydrophobic moiety. The final construct will then be labeled with $^{64}$Cu to form a myocardial perfusion PET agent in accordance with embodiments of the present invention.

Figure 5:
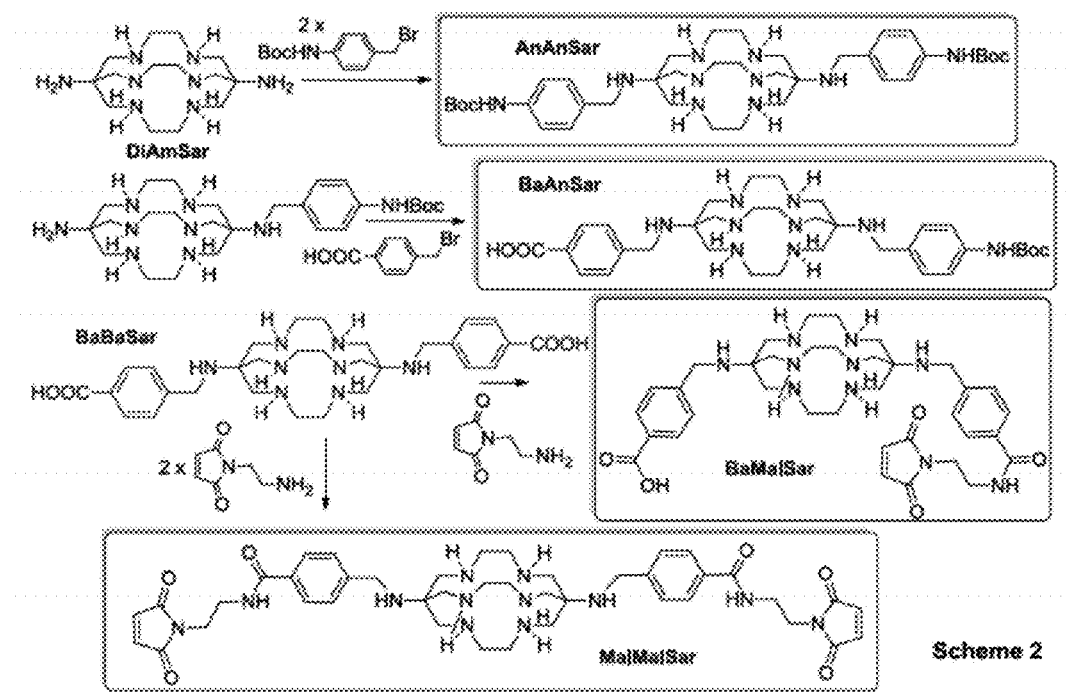
FIG. 5 shows exemplary synthetic schemes for making an $^{64}$Cu labeled PET MPI agents in accordance with embodiments of the present invention.

In order to attach the TPP ion and a hydrophobic moiety to the Sar bifunctional chelator, multifunctionalized Sar cage may be synthesized. The diamsar core (1, 8-Diamine-3, 6, 10, 13, 16, 19-hexaazabicyclo[6.6.6]icosane) contains a hexa-aza cage for $^{64}$Cu radiolabeling. Diamsar will be synthesized using established procedures in our laboratory and others. [14, 15] As the primary amines in DiAmSar are relatively inert, further derivatization is needed. Biological conjugation is generally achieved through three types of functional groups: amino group, carboxylic acid group, and sulfhydryl group. In addition to our newly developed BaBaSar (FIG. 2), [33] four exemplary radiolabelable cross-linking agents (AnAnSar, BaAnSar, BaMalSar, and MalMalSar) may be synthesized based on Sar backbone using the newly developed direct alkylation (SN2) method (Scheme 2 shown in FIG. 5).

For BaBaSar, the carboxylates may be activated and react with primary amines from TPP cation and the hydrophobic motif. Similar to BaBaSar, the free amino groups from AnAnSar will react with activated carboxylate groups in TPP cation and the hydrophobic motif to construct $^{64}$Cu PET MPI agent. MalMalSar is developed as a homo-functionalized agent that will react with sulfhydryl group. Based on these homo-functionalized agents, $^{64}$Cu labeled PET MPI probes will be constructed easily through thiol-Mal reaction.

Figure 6:
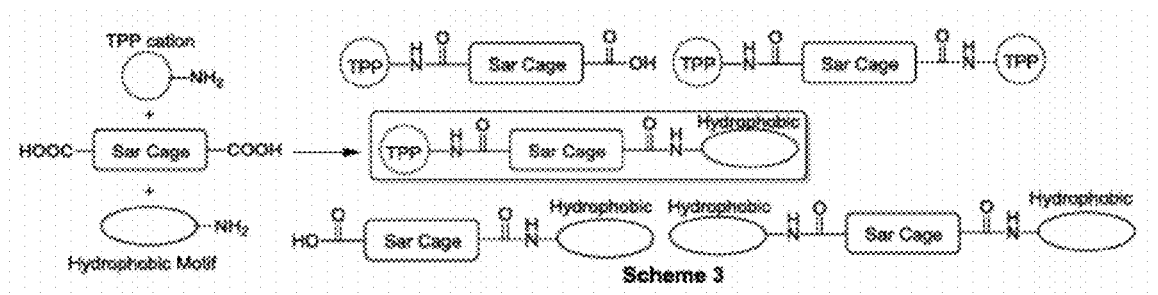
FIG. 6 shows another exemplary synthetic scheme for constructing an $^{64}$Cu labeled PET MPI agents in accordance with embodiments of the present invention.

For example, as shown in Scheme 3 (FIG. 6), the free carboxylate groups in BaBaSar may be activated with NHS/EDC followed by coupling with an amine in the TPP ion and an amine from the hydrophobic motif (such as long chain aliphatic amine). After coupling, the product must be purified (e.g. through HPLC) to remove the mono and the di-conjugated byproduct. The purified compound may be labeled with $^{64}$Cu for PET MPI evaluations. This method is straightforward (preferably just one step) and will be good for the construction of $^{64}$Cu-Sar-TPP agents. The di-TPP side products may also be tested as potential myocardial perfusion PET agents due to similar chemical structures. Using a similar approach, AnAnSar and MalMalSar may be used for the construction of $^{64}$Cu-Sar-TPP agents as well.

Figure 7:
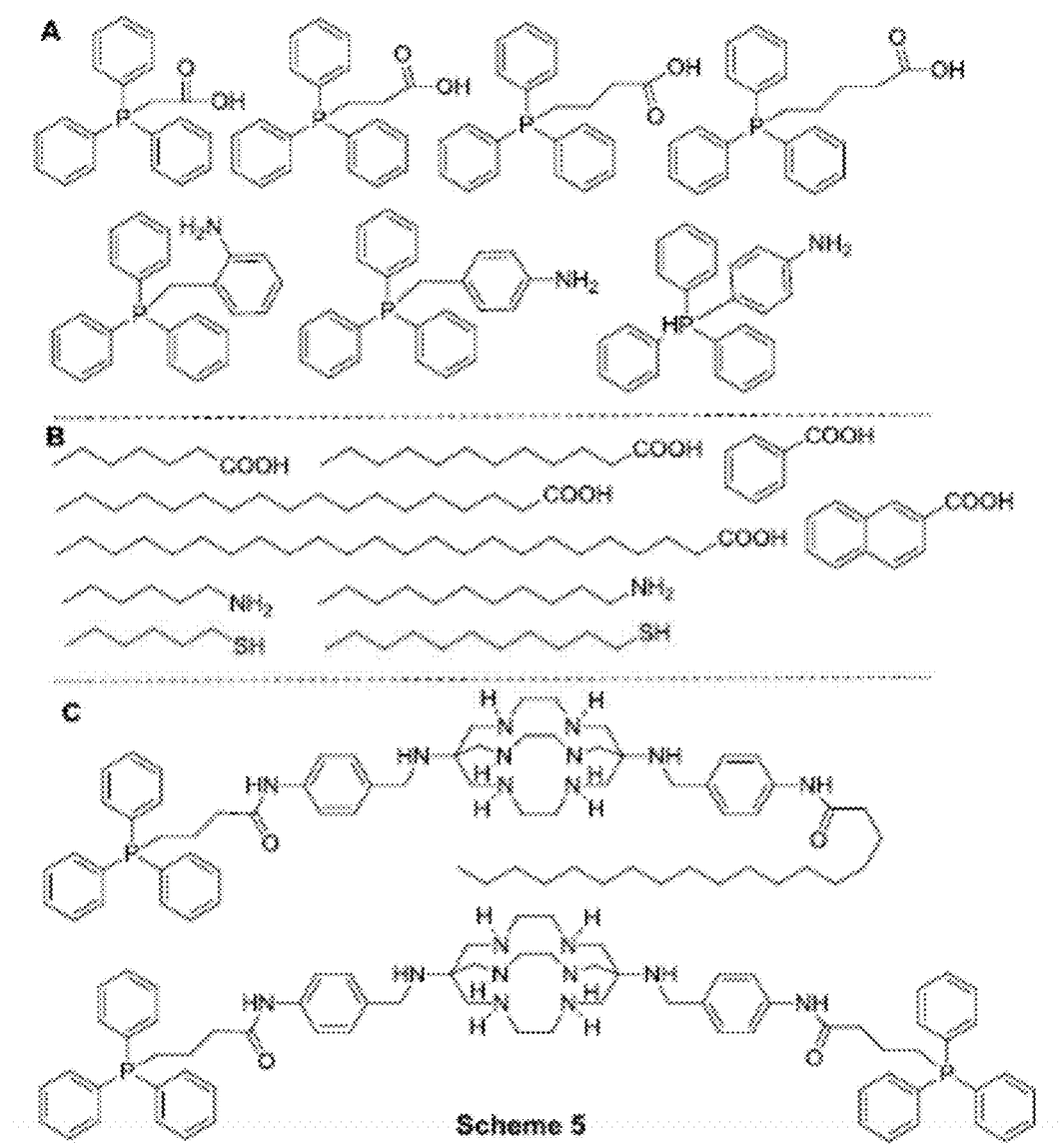
FIGS. 7 (A) and (B) shows an exemplary library of representative TPP cation and hydrophobic motif. (C) shows two representative MPI probes.

For hetero-functionalized agent BaAnSar, it may be used as a protected amino acid and incorporate this chelator to TPP cation and hydrophobic motif sequentially. Hetero-functionalized BaMalSar will be synthesized by converting one of the carboxylic acid groups in BaBaSar to maleimide group. This hetero functionalized ligand could give us better control of the reaction, which will lead to better yield of the $^{64}$Cu-Sar-TPP probes as shown in Scheme 4 (FIG. 7).

Construction of the $^{64}$Cu-Sar-TPP Probes

The homo-/hetero-functional Sar cages enable fast and simple construction of $^{64}$Cu-Sar-TPP probes. A series of $^{64}$Cu-Sar-TPP imaging probes may be synthesized based on our design. In our design, the TPP motif of the imaging probe will target mitochondria and help the retention of our imaging probe; the hydrophobic motif of the imaging probe will help the probe cross the membrane and reach the target. The liver uptake and clearance rate of the probe could be modified by this hydrophobic motif as well. The probes can be evaluated with in vitro assays before in vivo imaging experiments. Our $^{64}$Cu-Sar-TPP imaging probes can be divided into three parts: a TPP cation targeting mitochondria, a radiolabelable cross-linking agent based on Sar cage (Scheme 2), and a hydrophobic component. As shown in Scheme 5 (FIG. 7), a library of representative TPP cation and hydrophobic motif may be constructed. $^{64}$Cu-Sar-TPP imaging agents could then be easily synthesized as shown in scheme 3 and 4. Two representative MPI probes are shown in Scheme 5C. The first structure illustrates the example shown in Scheme 1. It carries one TPP cation for mitochondria targeting and one long aliphatic chain to increase hydrophobicity of the probe. The hydrophobicity of the probe will be fine-tuned by changing the length of the aliphatic chain or incorporating a benzyl or naphthyl motif. Multiple aliphatic chains could also be introduced to the molecule if there is a need. The second structure in Scheme 5C represents a potential di-cation MPI probe. Although the risk of this approach would be higher, the success of this method may lead to a superior MPI probe due to the increased zeta potential. A linker may need to be introduced between the TPP cation and the Sar cage to increase its hydrophobicity. The $^{64}$Cu labeling of these probes will be performed using the reported conditions (NH3Ac buffer, pH 5-5.5, 40 degree, 30 min incubation) [26].

The multifunctional Sar cages developed herein provide an attractive approach to construct $^{64}$Cu-Sar-TPP probes. Although the Sar cages only involve three commonly used functional groups, ligands bearing N3, alkyne, norbornene, tetrazine, cyclooctyne and cyclooctene may be alternatively used. Previously, DOTA conjugated TPP cation has been developed. However, those agents are not suitable for PET MPI due to the low cardinal uptake. In order to develop a suitable $^{64}$Cu MPI agent, we employed the positively charged Sar cage for Cu labelling. Unlike the traditionally used DOTA or NOTA chelators, the positively charged Sar chelator will maintain the zeta potential of the TPP probe for cardiac imaging. In addition, a hydrophobic motif may be introduced at the other end of the cage to help the probe cross membrane. A positively charged TPP agent with suitable hydrophobicity will lead to $^{64}$Cu labeled myocardial imaging probes.

In Vitro Methods Using $^{64}$Cu-Sar-TPP Analogues as Myocardial Perfusion PET Imaging Agents The $^{64}$Cu-Sar-TPP agent of the present invention will efficiently accumulate in heart by targeting mitochondria. The newly developed probes may be screened in vitro first to eliminate those compounds that are not suitable for in vivo imaging studies. microPET and biodistribution study on normal mice may then be performed for further evaluation. The most promising probe with high cardinal uptake, heart to liver, heart to lung, and heart to blood ratios may be evaluated in rats. These studies may lead to an optimized PET MPI probe.

Method

Stability Evaluation in Human Serum

Stability evaluations of $^{64}$Cu-Sar-TPP may be performed in human serum by radio-HPLC or radio-TLC analysis. For this in vitro stability test, $^{64}$Cu-Sar-TPP (0.37 MBq/100 µL) may be incubated with human serum (1.0 mL) in a 37° C. water bath for 0.5, 1, 2, 4, and 24 h. The samples may be analyzed by chromatography on ITLC-sg strips. After development, the chromatographic strips may be scanned on an automatic TLC scanner. Since the Sar cage could form extremely stable complex with $^{64}$Cu both in vitro and in vivo, the TPP cation should have reasonable stability at neutral pH or weak basic conditions (near physiology condition). $^{64}$Cu-Sar-TPP probes in accordance with embodiments of the present invention should also be stable in vitro and in vivo. Preferably the percentage of untouched compound is less than 90% after 24 h incubation.

Hydrophobicity Evaluation of $^{64}$Cu-Sar-TPP

To determine the lipophilicity of $^{64}$Cu-Sar-TPP, the compound may be dissolved in a mixture of 3 mL of saline (0.9% NaCl aqueous solution) and 3 mL of n-octanol in a round-bottom flask. The mixture is vigorously stirred for 20 min at room temperature and then transferred to a 15 mL Falcon conical tube. The tube is centrifuged at 3000 rpm for 5 min. Samples from n-octanol and aqueous layers are obtained and counted on a gamma counter. Log P value of $^{64}$Cu-Sar-TPP may be calculated based on this experiment. Although the optimal lipophilicity range is not available for the high myocardial selectivity of a radiotracer, a predictive model has been reported for selective accumulation of phosphonium cations in myocardial cells [34, 35]. For lipophilic cationic radiotracers, log P=0.5-1.5 (such as $^{99m}$Tc-sestamibi: log P=1.1) would render fast membrane diffusion kinetics, which would make them tend to localize in mitochondria-rich organs such as the heart. For $^{64}$Cu-Sar-TPP probes in accordance with embodiments of this invention, the hydrophobic motif will increases the interaction between TPP cation and the lipid core, due to the hydrophobicity of the lipophilic phosphonium cation and increased entropy.

The $^{64}$Cu-Sar-TPP probe preferably has a log P value ranging from 0.5 to 1.5 because the one with lower log P may not efficiently cross the membrane and the one with higher log P may result in high liver uptake.

Transport Studies

Uptake kinetics of $^{64}$Cu-Sar-TPP and 3H-TPP (standard) may be examined in H345 lung carcinoma cells. In brief, H345 cells will be harvested by trypsinization and washed twice with cold PBS buffer. Cells are counted and re-suspended in loading buffer at a concentration of 2×106 cells/mL. The cell suspension (0.5 mL) may be transferred to Eppendorf tubes and incubated at 37° C. for 60 min. An equal volume of loading solution containing 0.5-5 nM $^{64}$Cu-Sar-TPP and 3H-TPP will be added. The sample may be centrifuged (800 rpm, 5 min) to terminate the uptake. Aliquots of the supernatant are then obtained and the remaining solution is aspirated. The radioactivity of the pellet and supernatant is counted together with standard solution (1/1,000) in a gamma counter. After completion of gamma counting, scintillation counting are performed after the complete decay of $^{64}$Cu (two weeks). Cell uptake values of $^{64}$Cu-Sar-TPP in H345 cells may be determined over incubation periods of 0.5, 1, 2, 4, and 24 h. The uptake value may be compared with 3H-TPP to study the effect on TPP uptake after introducing Sar cage and hydrophobic motif. The mitochondrial membrane potential-dependent cellular uptake of $^{64}$Cu-Sar-TPP will be further assessed using the H345 cells treated with carbonyl cyanide m-chlorophenylhydrazone (CCCP). The weak acid protonophore CCCP uncouples mitochondria by selectively abolishing the inner mitochondrial membrane potential. Cells may be incubated for 10 min with CCCP, prior to adding $^{64}$Cu-Sar-TPP and 3H-TPP to the loading buffer. CCCP will produce a dose dependent decrease in cell-associated activity. Only the $^{64}$Cu-Sar-TPP probes that are sensitive towards CCCP will be evaluated in future investigation because this experiment supports the tracer uptakes are depend on mitochondria potential as we proposed above.

Figure 8:
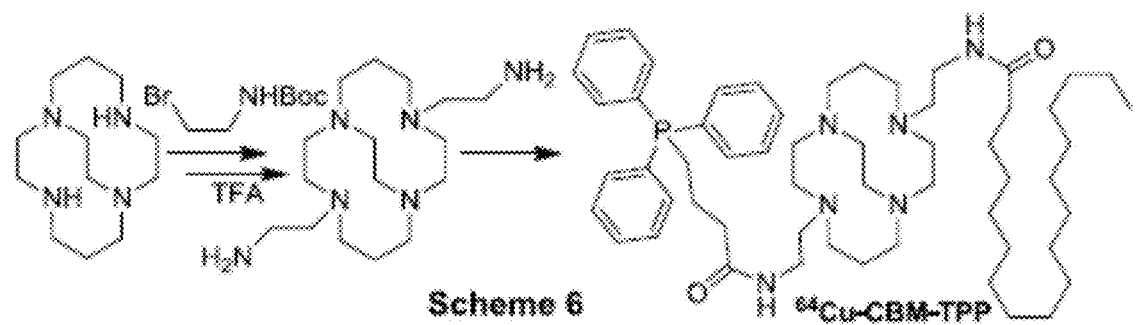
FIG. 8 shows the preparation of an exemplary tracer $^{64}$Cu-CBM-TPP in accordance with one embodiment of the present invention.

Alternatively, the cross-bridge tetra-amine ligands are another new type of positively charged chelator for complexing $^{64}$Cu [15, 36]. The preparation of a second tracer $^{64}$Cu-CBM-TPP is shown in Scheme 6 (FIG. 8). $^{64}$Cu-CBM-TPP may be purified and characterized by radio-TLC and HPLC. The biological evaluation experiments are the same as proposed above.

MicroPET/CT and Quantitative Autoradiagraphy Imaging Methods Using $^{64}$Cu-Sar-TPP Analogues in Animals After in vitro screening, promising candidates may be obtained, which may be further evaluated in vivo in mice. The criteria for a good $^{64}$Cu-Sar-TPP probe includes high cardinal uptake, good stability in vivo, and high heart to muscle, heart to liver, heart to lung, and heart to blood ratios. The selected probes may be further evaluated in rats including a side by side comparison with established $^{13}$N—NH$_3$ and $^{99m}$Tc-Sestamibi agents.

Method

In Vivo and Ex Vivo Characterization of $^{64}$Cu-Sar-TPP Pharmacokinetics in Mice The in vivo kinetics of the $^{64}$Cu-Sar-TPP will be evaluated in normal mice. PET imaging will be conducted with a microPET P4 system (Concorde Microsystems Incorporated, Knoxville, Tenn., USA). Dynamic PET imaging will initiate concurrently with intravenous administration of 0.2-0.3 mCi (7.4-11.1 MBq)$^{64}$Cu-Sar-TPP via the tail vein. The scan duration and frame rates are 20 s×3, 40 s×3, 60 s×2, 120 s×2, 240 s×5 and 300 s×6, for a total time of 60 min. Static scans may be performed at 2, 4, 8, and 24 h post injection. For each scan, regions of interest (ROIs) are to be drawn over heart, normal tissue, and major organs on decay-corrected whole-body coronal images. For PET scans, the ROIs may be converted percentage administered activity per gram of tissue (% ID/g). At the completion of the PET study, animals may be sacrificed, selected organs (blood, brain, heart, lung, liver, spleen, kidney, and muscle) may be excised, and radioactivity may be counted in a gamma counter together with the standards (1/100). Radioactivity may be expressed as percentage of injected dose per gram tissue (% ID/g). The in vivo biodistribution of $^{64}$Cu-Sar-TPP could help us select the potential MPI probes with high levels of radioactivity accumulated in the heart. The optimal tracer should have rapid clearance from the blood, which will lead to high heart-to-blood ratio. The heart-to-lung and heart-to-liver ratio are other important criteria for selecting an optimal cardiac imaging agent.

Metabolic Stability Study.

The metabolic stabilities of $^{64}$Cu-Sar-TPP may be evaluated in an athymic nude mouse. Two hours after intravenous injection of 11.1 MBq of $^{64}$Cu-Sar-TPP, the mouse will be sacrificed and relevant organs will be harvested. The blood is collected immediately and centrifuged for 5 min at 14,000 rpm. 50% TFA in 100 uL PBS is added to the upper serum solution, followed by mixing and centrifugation for 5 min. The upper solution may then be taken and injected for HPLC analysis. Liver, kidneys, and heart may be homogenized using a homogenizer, suspended in 1 mL of PBS buffer, and then centrifuged for 5 min at 14,000 rpm, respectively. For each sample, after removal of the supernatant, 50% TFA in 100 uL PBS may be added to the solution, followed by mixing and centrifugation for 5 min. The upper solution may then be taken and injected for HPLC analysis. The eluent may be collected with a fraction collector (1.5 min/fraction) and the radioactivity of each fraction will be measured with the γ-counter. A $^{64}$Cu-Sar-TPP probe with good in vivo stability will be prioritized for further studies.

Preparation of the Rat Models with Myocardial Perfusion Deficit

Rats (male Sprague-Dawley, aged 8-10 weeks, with body weight of 300-400 g) may be anesthetized, intubated, and ventilated according to known methods in the art [37]. A left thoracotomy may be performed to expose the heart. In order to create a no-flow zone, the left coronary artery may be permanently ligated. In order to develop an ischemia-reperfusion injury (n=20), the left coronary artery may be ligated for 30 minutes, followed by a 120-minute reperfusion.

In Vivo Biodistribution of $^{64}$Cu-Sar-TPP in Normal Rats and Rat Models with Myocardial Perfusion Deficit Once an optimal $^{64}$Cu-Sar-TPP agent is identified from the mouse based studies, we will perform the in vivo tissue biodistribution study in normal rats and rat models with a myocardial perfusion deficit (3 rats/tracer). After anesthetization, the rats may be intravenously injected with $^{64}$Cu-Sar-TPP. Blood samples may be drawn at 0.5, 1, 2, 4, or 24 hours post-injection to study the clearance of the probe. microPET imaging may be performed at these time points as well. Animals may be sacrificed via $CO_2$ at 24 hours post-injection. Blood, heart, liver, kidney, lung and other major organs and tissues will be collected, wet weighed, and counted in a y-counter (Packard). Percent injected dose per gram (% ID/g) may be calculated by the comparison with standards representing the injected dose per animal. Values may be quoted as mean±standard deviation (SD) and the results of $^{64}$Cu-Sar-TPP on normal rats will be compared with that on rats with myocardial perfusion deficits. Quantitative autoradiography will be used to assess the cardiac uptake of these tracers according to literatures procedures [38, 39]. As reference agents, $^{13}$N-Ammonia and $^{99m}$Tc-Sestamibi will be tested in these models as well. Animals may first be scanned up to 1 h post injection with microPET after the injection of $^{13}$N—NH3. microSPECT scan may be performed using $^{99m}$Tc-Sestamibi. The microPET/CT (for $^{64}$Cu-Sar-TPP, $^{13}$N-Ammonia) or microSPECT/CT (for $^{99m}$Tc-Sestamibi) image data may be produced after analysis and reconstruction. The imaging derived data of normal rat groups and model rat groups may be compared, along with the results of the corresponding tissue biodistribulion studies. The side-by-side comparison between $^{64}$Cu-Sar-TPP with the established $^{13}$N—NH$_3$ and $^{99m}$Tc-Sestamibi agents may reveal the advantages and limitations of each probes.

Unlike commonly used PET MPI agents, the $^{64}$Cu-TPP probes can not only overcome the production and protocol limitations of currently used radiotracers, but also allow delayed cardiac imaging following administration, which may provide critical information that could not be obtained before. However, the difference in radioisotope half-life would also lead to radiation exposure variation. In this example, we did not perform the dosimetry calculation at the early research and development stage. Once an optimized probe is identified, a careful radiation dosimetry and toxicity study would be necessary. As $^{64}$Cu labeled compounds have been successfully tested in clinic, the above concerns should not limit the translation of our $^{64}$Cu PET MPI agents.

In cases where compounds of the present invention are ionic or otherwise sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, a-ketoglutarate, and a-glycerophosphate. Suitable inorganic salts may also be formed, including hydrochloride, sulfate, nitrate, bicarbonate, and carbonate salts.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Pharmaceutically acceptable salts may be obtained using standard procedures well known in the art, for example by reacting a sufficiently basic compound such as an amine with a suitable acid affording a physiologically acceptable anion. Alkali metal (e.g., sodium, potassium or lithium) or alkaline earth metal (e.g., calcium) salts of carboxylic acids can also be made.

The compositions may also be present as a solvate or hydrate. As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

Prior to administration to a patient, the $^{64}$Cu-Sar-TPP compositions of the present invention are generally dissolved or dispersed in an appropriate carrier. As such, the present inventions include pharmaceutical compositions comprising a $^{64}$Cu-Sar-TPP analog dissolved or dispersed in a carrier. "Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

In connection with the methods of PET imaging, the pharmaceutical compositions are generally administered in an effective amount. An "effective amount" of the pharmaceutical compositions is an amount sufficient to carry out a specifically stated purpose. An "effective amount" may be determined empirically and in a routine manners in relation to the stated purpose.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Those skilled in the art will recognize, or be able to ascertain using no more than routine experimentation, many equivalents to the specific embodiments of the method and compositions described herein. Such equivalents are intended to be encompassed by the following claims.

REFERENCES

The following references are each relied upon and incorporated herein by reference in their entirety:

1. Rischpler C, Park M J, Fung G S, Javadi M, Tsui B M, Higuchi T. Advances in PET myocardial perfusion imaging: F-18 labeled tracers. Ann Nucl Med. 2011.
2. Beller G A, Bergmann S R. Myocardial perfusion imaging agents: SPECT and PET. J Nucl Cardiol. 2004; 11:71-86.
3. Furer V, Fayad Z A, Mani V, Calcagno C, Farkouh M E, Greenberg J D. Noninvasive Cardiovascular Imaging in Rheumatoid Arthritis: Current Modalities and the Emerging Role of Magnetic Resonance and Positron Emission Tomography Imaging. Semin Arthritis Rheum. 2011.
4. Naresh N K, Ben-Mordechai T, Leor J, Epstein F H. Molecular Imaging of Healing After Myocardial Infarction. Curr Cardiovasc Imaging Rep. 2011; 4:63-76.
5. Thompson D, Koster M J, Wagner R H, Heroux A, Barron J T. Single photon emission computed tomography myocardial perfusion imaging to detect cardiac allograft vasculopathy. Eur J Echocardiogr. 2011.
6. Bybee K A, Lee J, Markiewicz R, Longmore R, McGhie A I, O'Keefe J H, et al. Diagnostic and clinical benefit of combined coronary calcium and perfusion assessment in patients undergoing PET/CT myocardial perfusion stress imaging. J Nucl Cardiol. 2010; 17:188-96.
7. Di Carli M F, Dorbala S, Meserve J, El Fakhri G, Sitek A, Moore S C. Clinical myocardial perfusion PET/CT. J Nucl Med. 2007; 48:783-93.
8. Slomka P J, Alexanderson E, Jacome R, Jimenez M, Romero E, Meave A, et al. Comparison of Clinical Tools for Measurements of Regional Stress and Rest Myocardial Blood Flow Assessed with 13N-Ammonia PET/CT. J Nucl Med. 2012.
9. Heller G V, Calnon D, Dorbala S. Recent advances in cardiac PET and PET/CT myocardial perfusion imaging. J Nucl Cardiol. 2009; 16:962-9.
10. Maddahi J, Czernin J, Lazewatsky J, Huang S C, Dahlbom M, Schelbert H, et al. Phase I, first-in-human study of BMS747158, a novel 18F-labeled tracer for myocardial perfusion PET: dosimetry, biodistribution, safety, and imaging characteristics after a single injection at rest. J Nucl Med. 2011; 52:1490-8.
11. Nekolla S G, Reder S, Saraste A, Higuchi T, Dzewas G, Preissel A, et al. Evaluation of the novel myocardial perfusion positron-emission tomography tracer 18F-BMS-747158-02: comparison to 13N-ammonia and validation with microspheres in a pig model. Circulation. 2009; 119:2333-42.
12. Higuchi T, Fukushima K, Rischpler C, Isoda T, Javadi M S, Ravert H, et al. Stable delineation of the ischemic area by the PET perfusion tracer 18F-fluorobenzyl triphenyl phosphonium after transient coronary occlusion. J Nucl Med. 2011; 52:965-9.
13. Madar I, Huang Y, Ravert H, Dalrymple S L, Davidson N E, Isaacs J T, et al. Detection and quantification of the evolution dynamics of apoptosis using the PET voltage sensor 18F-fluorobenzyl triphenyl phosphonium. J Nucl Med. 2009; 50:774-80.
14. Madar I, Ravert H, Dipaula A, Du Y, Dannals R F, Becker L. Assessment of severity of coronary artery stenosis in a canine model using the PET agent 18F-fluorobenzyl triphenyl phosphonium: comparison with 99mTc-tetrofosmin. J Nucl Med. 2007; 48:1021-30.
15. Wadas T J, Wong E H, Weisman G R, Anderson C J. Copper chelation chemistry and its role in copper radiopharmaceuticals. Curr Pharm Des. 2007; 13:3-16.
16. Wallhaus T R, Lacy J, Whang J, Green M A, Nickles R J, Stone C K. Human biodistribution and dosimetry of the PET perfusion agent copper-62-PTSM. J Nucl Med. 1998; 39:1958-64.
17. Smith R A, Hartley R C, Murphy M P. Mitochondria-targeted small molecule therapeutics and probes. Antioxid Redox Signal. 2011; 15:3021-38.
18. Shoup T M, Elmaleh D R, Brownell A L, Zhu A, Guerrero J L, Fischman A J. Evaluation of (4-[18F] Fluorophenyl)triphenylphosphonium ion. A potential myocardial blood flow agent for PET. Mol Imaging Biol. 2011; 13:511-7.
19. Madar I, Ravert H, Nelkin B, Abro M, Pomper M, Dannals R, et al. Characterization of membrane potential-dependent uptake of the novel PET tracer 18F-fluorobenzyl triphenylphosphonium cation. Eur J Nucl Med Mol Imaging. 2007; 34:2057-65.
20. Ravert H T, Madar I, Dannals R F. Radiosynthesis of 3-[18F]fluoropropyl and 4-[18F]fluorobenzyl triarylphosphonium ions. Journal of Labelled Compounds and Radiopharmaceuticals. 2004; 47:469-76.
21. Flewelling R F, Hubbell W L. Hydrophobic ion interactions with membranes. Thermodynamic analysis of tetraphenylphosphonium binding to vesicles. Biophys J. 1986; 49:531-40.
22. Ross M F, Kelso G F, Blaikie F H, James A M, Cocheme H M, Filipovska A, et al. Lipophilic triphenylphosphonium cations as tools in mitochondrial bioenergetics and free radical biology. Biochemistry (Mosc). 2005; 70:222-30.
23. James A M, Cocheme H M, Smith R A, Murphy M P. Interactions of mitochondria-targeted and untargeted ubiquinones with the mitochondrial respiratory chain and reactive oxygen species. Implications for the use of exogenous ubiquinones as therapies and experimental tools. J Biol Chem. 2005; 280:21295-312.
24. James A M, Sharpley M S, Manas A R, Frerman F E, Hirst J, Smith R A, et al. Interaction of the mitochondria-targeted antioxidant MitoQ with phospholipid bilayers and ubiquinone oxidoreductases. J Biol Chem. 2007; 282:14708-18.
25. Ross M F, Prime T A, Abakumova I, James A M, Porteous C M, Smith R A, et al. Rapid and extensive uptake and activation of hydrophobic triphenylphosphonium cations within cells. Biochem J. 2008; 411:633-45.
26. Cai H, Li Z, Huang C W, Shahinian A H, Wang H, Park R, et al. Evaluation of copper-64 labeled AmBaSar conjugated cyclic RGD peptide for improved microPET imaging of integrin alphavbeta3 expression. Bioconjug Chem. 2010; 21:1417-24.
27. Huang C W, Li Z, Cai H, Shahinian T, Conti P S. Biological stability evaluation of the alpha2beta1 receptor imaging agents: diamsar and DOTA conjugated DGEA peptide. Bioconjug Chem. 2011; 22:256-63.
28. Ma M T, Karas J A, White J M, Scanlon D, Donnelly P S. A new bifunctional chelator for copper radiopharmaceuticals: a cage amine ligand with a carboxylate functional group for conjugation to peptides. Chem Commun (Camb). 2009:3237-9.
29. Donnelly P S, Harrowfield J M, Skelton B W, White A H. Carboxymethylated cage amines: coordination and lactamization. Inorg Chem. 2001; 40:5645-52.

30. Cai H, Li Z, Huang C W, Park R, Shahinian A H, Conti P S. An improved synthesis and biological evaluation of a new cage-like bifunctional chelator, 4-((8-amino-3,6,10,13,16,19-hexaazabicyclo[6.6.6]icosane-1-ylamino)methyl)benzoic acid, for 64Cu radiopharmaceuticals. Nucl Med Biol. 2010; 37:57-65.

31. Liu S, Li Z, Yap L P, Huang C W, Park R, Conti P S. Efficient preparation and biological evaluation of a novel multivalency bifunctional chelator for 64Cu radiopharmaceuticals. Chemistry. 2011; 17:10222-5.

32. Di Bartolo N M, Sargeson A M, Donlevy T M, Smith S V. Synthesis of a new cage ligand, SarAr, and its complexation with selected transition metal ions for potential use in radioimaging. J Chem Soc Dalton. 2001:2303-9.

33. Liu S, Li Z, Yap L P, Huang C W, Park R, Conti P S. Efficient preparation and biological evaluation of a novel multivalency bifunctional chelator for (64)Cu radiopharmaceuticals. Chemistry. 2011; 17:10222-5.

34. Zhou Y, Kim Y S, Shi J, Jacobson O, Chen X, Liu S. Evaluation of 64Cu-labeled acridinium cation: a PET radiotracer targeting tumor mitochondria. Bioconjug Chem. 2011; 22:700-8.

35. Liu S. Ether and crown ether-containing cationic 99mTc complexes useful as radiopharmaceuticals for heart imaging. Dalton Trans. 2007:1183-93.

36. Sprague J E, Peng Y, Fiamengo A L, Woodin K S, Southwick E A, Weisman G R, et al. Synthesis, characterization and in vivo studies of Cu(II)-64-labeled cross-bridged tetraazamacrocycle-amide complexes as models of peptide conjugate imaging agents. J Med Chem. 2007; 50:2527-35.

37. Yu M, Guaraldi M T, Mistry M, Kagan M, McDonald J L, Drew K, et al. BMS-747158-02: a novel PET myocardial perfusion imaging agent. J Nucl Cardiol. 2007; 14:789-98.

38. Crane P D, Onthank D C, Bourque C R, Heminway S J, Mazaika T J, Leav I, et al. Autoradiography and radioscintigraphy of technetium-99m-sestamibi in c-neu transgenic mice. J Nucl Med. 1995; 36:1862-8.

39. Wu J C, Inubushi M, Sundaresan G, Schelbert H R, Gambhir S S. Positron emission tomography imaging of cardiac reporter gene expression in living rats. Circulation. 2002; 106:180-3.

What is claimed is:

1. A multi-unit molecule useful as an imaging tracer, comprising:
    one or more cationic units;
    one or more hexaaza sacophogine cage (sar) multifunctional chelator units; and
    one or more hydrophobic units,
    wherein said one or more cationic units, one or more sar multifunctional chelator units and one or more hydrophobic units may be linked directly to each other or via a linker arranged in any sequential order in a linear linkage,
    wherein said one or more cationic units is selected from the group consisting of TPP, —P⁺R₁R₂R₃ and —N⁺R₁R₂R₃, wherein R₁, R₂, and R₃ are each independently selected from an optionally substituted aryl, an optionally substituted aralkyl, an optionally substituted alkyl, an optionally substituted cycloalky, or an optionally substituted heteroaryl, wherein said one or more sar multifuncitional chelator units is one selected from the group consisting of BaBaSar, AnAnSar, BaAnSar, BaMalSar, and MalMalSar,
    wherein said one or more hydrophobic units is selected from the group consisting of:

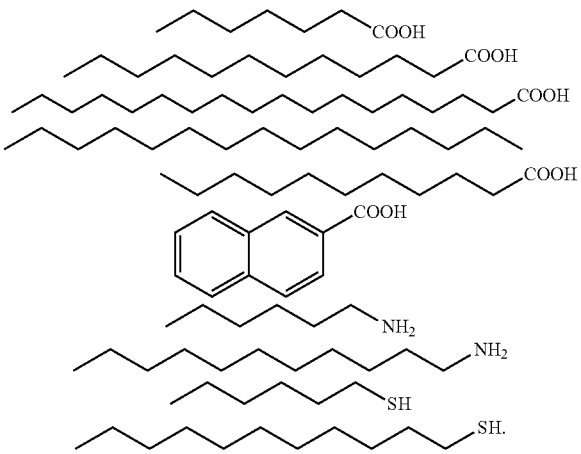

2. The multi-unit molecule of claim 1, wherein said one or more sar multifuncitional chelator units is complexed with ⁶⁴Cu, ⁶⁸Ga, or an equivalent thereof.

3. The multi-unit molecule of claim 1, wherein said one or more sar multifunctional chelator units is functionalized with at least one of N3, alkyne, norbornene, tetrazine, cyclooctyne and cyclooctene.

4. A method of imaging a subject's heart, comprising:
    administering a composition containing an effective amount of the multi-unit molecule according to claim 2; and
    taking images of the subject's heart using a suitable imaining device.

5. A method of forming a imaging tracer of claim 1, useful as a PET tracer for myocardial perfusion imaging, comprising:
    linking one or more cationic units and one or more hydrophobic units to one or more hexaaza sacophogine cage (sar) multifunctional chelator units in a linear arrangement to form a multi-unit molecule, wherein said units may be linked to each other directly or via a linker in any sequential order; and
    labeling said multi-unit molecule with a suitable radioactive isotope selected from ⁶⁴Cu, ⁶⁸Ga, or equivalents thereof.

6. An imaging reagent kit, comprising:
    a composition containing a multi-unit molecule according to claim 1, wherein said multi-unit molecule further includes a ⁶⁴Cu label; and
    an instruction for producing and administering an imaging tracer using said composition.

* * * * *